(12) United States Patent
Jung et al.

(10) Patent No.: US 7,083,811 B2
(45) Date of Patent: Aug. 1, 2006

(54) HERBAL COMPOSITION FOR THE PREVENTION AND TREATMENT OF DEMENTIA

(75) Inventors: Kyu Yong Jung, 306-503 Shinan Apt., Kwonsun-dong 1235, Kwonsun-ku, Suwon, Syunggi-do (KR); Kyung Soo Keum, 683-6 Namsan 1-dong, Chung-ku, Daegu (KR)

(73) Assignees: Siloam Hightech Pharm. Co., Ltd., Seoul (KR); Kyu Yong Jung, Seoul (KR); Kyung Soo Keum, Seoul (KR)

( * ) Notice: Subject to any disclaimer, the term of this patent is extended or adjusted under 35 U.S.C. 154(b) by 42 days.

(21) Appl. No.: 10/053,620

(22) Filed: Jan. 24, 2002

(65) Prior Publication Data

US 2003/0003167 A1    Jan. 2, 2003

Related U.S. Application Data

(63) Continuation-in-part of application No. 09/850,269, filed on May 8, 2001.

(30) Foreign Application Priority Data

Feb. 8, 2001    (KR) .................................. 2001-6177

(51) Int. Cl.
*A61K 35/78*    (2006.01)

(52) U.S. Cl. ...................... 424/725; 424/736; 424/756; 424/773; 424/774; 424/778; 424/779

(58) Field of Classification Search ................ 424/725, 424/736, 756, 773, 774, 778, 779
See application file for complete search history.

(56) References Cited

U.S. PATENT DOCUMENTS 5,466,443 A * 11/1995 Ho et al.
5,707,631 A * 1/1998 Lieberman
5,916,555 A * 6/1999 Lee et al.
6,010,702 A   1/2000 Lee et al.

FOREIGN PATENT DOCUMENTS

JP    06056684 A  *  3/1994
JP    07025777 A  *  1/1995
JP    07179342 A  *  7/1995

OTHER PUBLICATIONS

Internet description of GERIFORTE tablets ((<<www.eisra.nl/gb/complex/geriforte.htm>>) (1998)).*
Derwent English abstract of Chinese Pat. Appl. No. 1207942 A (1999).*
E. Giacobini, "Modulation of Brain Acetylcholine Levels with Cholinestrase Inhibitors as a Treatment of Alzheimer Disease", Keio J. Med., vol. 36, pp. 381-391, (1987).
J.A. Christie et al., "Physostigmine and Arecoline: Effects of Intravenous Infusions in Alzheimer Presenile Dementia", Brit. J. Psychiat. vol. 138, pp. 46-50 (1981).
W.K. Summers et al., "Oral Tetrahydroaminoacridine in Logn-Term Treatment of Senile Dementia Alzheimer Type", The New England Journal of Medicine, vol. 315, No. 20, pp. 1241-1245, (1986).
G.L. Ellman, et al., "A New and Rapid Coloimetric Determination of Acetylcholinesterase Activity", Biochemical Pharmacology, vol. 7, pp. 88-95, (1961).
W.Fetrow et al., Professional's Handbook of Complementary and Alternative Medicines, pp. 282-291 (1999).

* cited by examiner

*Primary Examiner*—Susan D. Coe
(74) *Attorney, Agent, or Firm*—Finnegan, Henderson, Farabow, Garrett & Dunner, LLP

(57) ABSTRACT

The present invention relates to herbal composition for the prevention and treatment of dementia comprising *Polygoni multiflori Radix* (*Polygonum multiflorum* Thunberg), instead of ginseng, *Polygalae Radix* (*Polygala tatarinowi* Regel), *Caryophylli Flos* (*Eugeni caryophyllata* Thunberg), and *Zingibreis Rhizoma* (*Zingiber officinale* Rosc.) in the conventional herbal composition to maximize anti-dementia effect with minimized amount.

3 Claims, 6 Drawing Sheets

HERBAL COMPOSITION FOR THE PREVENTION AND TREATMENT OF DEMENTIA

BACKGROUND OF THE INVENTION

The present invention is a continuation-in-part of U.S. patent application, Ser. No. 09/850,269, filed May 8, 2001.

1. Field of the Invention

The present invention relates to a herbal composition for the treatment of dementia comprising *Polygoni multiflori Radix* (*Polygonum multiflorum* Thunberg) as a Principal Drug, or main component. Oriental Medicine conventionally treats dementia with ginseng as a Principal Drug. The herbal composition of the invention is efficacious against dementia, especially senile dementia, and demonstrates improved pharmacological and clinical properties, as well as fewer adverse effects, compared to conventional products.

2. Description of the Related Art

Recently the magnitude of the dementia problems as well as senile dementia has been rapidly increased. To date, dementia has no known prevention or cure except several treatment drugs showing extremely limited effects toward dementia, although there have been intensive studies in the development of drugs or foods to prevent or cure dementia in eastern or western countries. Still intensive researches have focused on senile dementia and Alzheimer's disease (AD), which refer to "progressive loss of cognition and intellectual abilities, in the biochemical, genetic and medical aspects. More specifically, main symptoms of dementia include cognitive function impairment and various mental disorders in language, judgment and perceptive vasospastic ability as well as serious difficulty in acquisition of new technologies. Personality changes and emotional restlessness soon become apparent and ultimately to death Dementia, which adversely affects the intrinsic activity of cerebrum, is a peculiar symptom associated with the fundamental disorders of brain induced by various factors. For example, the brain was grossly shrunken in size and the expansion of the ventricle in most cases due to loss of cerebral parenchyma, a large number of cerebral cortex cells, Purkinje cells in cerebellum or eukaryotic cells at spinal cord become disappeared. The causes of these symptoms are unknown but they have been noticed to have significant relations with the level of neurotransmitter acetylcholine (ACh).

Commercially available anti-dementia agents include Cognex and Done Pezyl, which are known to inhibit the activity of acetylcholinesterase (AChE) acting to the cereboneuronal system, thus increasing the level of cerebral acetylcholine contents, followed by improvement and treatment of cholinergic dysfunctions including dementia.

However, a majority of the conventional anti-dementia agents may produce serious cholinergic effects in the peripheral nerve with an extremely short half-life and severe side effects such as hepatotoxicity (*Br. J. Psychiatry*, 138, 46, 1981). Further, Cognex (9-amino-1,2,3,4-tetrahydroacridine, THA), which have been widely used for the treatment of dementia, is effective significantly in enhancement of cognitive ability in AD patients during oral administration (*N, Engl. J. Med.*, 315, 1241, 1986) but many adverse reactions such as tremor, dizziness and cytotoxicity have still encountered. Therefore, elevating the level of the ACh can be another pharmacological concept to prevent or cure of dementia by improving the metabolism of cholinergic pathway as well as inhibiting the AchE activity.

On the other hand, Korean Patent Publication No. 1999-85202 which is the corresponding patent of U.S. Pat. No. 6,010,702 discloses herbal extracts having ginseng as a major component to inhibit against AChE activity with less severe side effects.

These herbal extracts show some effects toward dementia but they are not reliably effective. And it is only expected that the action mechanism of the herbal extracts is different from that of other dementia agents, although the herbal extracts showed some effects for senile dementia. In particular, the use of ginseng, which is a major component of the conventional herbal composition, leads to some adverse reactions such as palpitation of the heart and functional homeostatic imbalance for patients with cardiovascular diseases. Ginseng is widely known to recover intrinsic energy but it will be prohibited from using ginseng as an anti-dementia agent by the following reasons reported in the literature.

Ginseng may deprave the symptoms of patients who suffer from hypernoia, nervous prostration, hypertension or arteriosclerosis due to its side effects. And further, it is well known in oriental medicine theory that ginseng should not be used to patients suffering from pulmonary tuberculosis, asthma and cough (*Professional's Handbook of Complementary and Alternative medicines,* Charles W. Fetrow and Juan R. Avila, 1999, p 282–291) and recently, there are clinical reports suspecting its use.

Furthermore, compositions of such herbal extracts are administered with relatively excess amount, resulting in unexpected side effects and toxicities therefrom.

SUMMARY OF THE INVENTION

Even though the herbal extracts show less side effects compared to other drugs, there are not enough clinical studies about exact therapeutic efficacy and side effects. Therefore, it is still strongly demanded to develop more effective herbal extracts. In order to supply herbal extracts to general publics as health foods for the prevention and treatment of dementia, it will be more important to minimize both dose amount and side effects.

Under this circumstance, the inventor has developed the first herbal extract composition registered in the US (U.S. Pat. No. 6,010,072) for the treatment of dementia and further made intensive studies to develop a novel herbal drug having an inhibitory action on AChE with little adverse reactions mentioned above and under the judgment that a drug containing some herbs may lessen any adverse reactions and has an inhibitory action on AChE. As a result of repeated the efficacy screening and toxicity tests in a composition where some supplemental herbs are added to the conventional herbal extracts having an inhibitory action on AChE, it has been confirmed that the herbal composition of this invention has superior effects in the prevention and treatment of dementia by improving blood-circulation disturbance and facilitating the glucose metabolism in the neurons. In consequence, the inventor has completed this invention.

Therefore, an object of the present invention is to provide superior herbal composition for the prevention and treatment of dementia having improved pharmacological and clinical properties compared to the conventional herbal composition by replacing ginseng with *Polygoni multiflori Radix* (*Polygonum multiflorum* Thunberg) as a main component to the conventional composition.

BRIEF DESCRIPTION OF THE DRAWINGS

The above object and feature of the present invention will become apparent from the following description of the invention, when taken in conjunction with the accompanying drawings, in which.

DETAILED DESCRIPTION OF THE INVENTION

Figure 1:
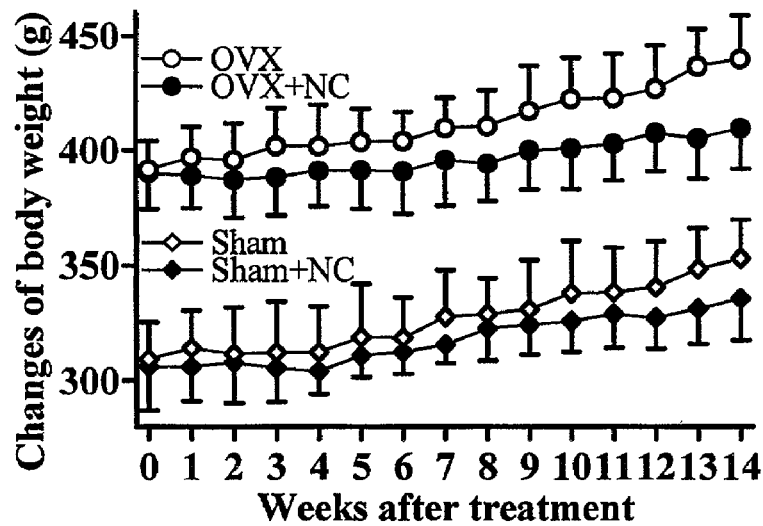
FIG. 1 represents changes of body weights in sham and OVX rats, where results were expressed as mean±S.E. from 10 rats (*p<0.05 versus OVX with treatment)

The present invention provides an herbal extract composition comprising 10–50 weight parts of *Polygoni multiflori Radix* (*Polygonum multiflorum* Thunberg) and at least three components chosen from 5–20 weight parts of *Poria* (*Poria cocos* (Schw.) Wolf), 2–20 weight parts of *Aurantii nobilis Pericarpium* (*Citrus unshiu* Marco.), 1–5 weight parts of *Glycyrrhizae Radix* (*Glycyrrhiza uralensis* Fischer), 1–10 weight parts of *Pinelliae Tuber* (*Pinellia ternata* Tenor et Breitenbach), and 1–10 weight parts of *Zingibreis Rhizoma* (*Zingiber officinale* Rosc.).

The herbal composition of the present invention may further comprise at least one component chosen from 1–10 weight part of *Polygalae Radix* (*Polygala tatarinowi* Regel), 1–10 weight parts of *Caryophylli Flos* (*Eugenia caryophyllata* Thunberg), 1–15 weight parts of *Arisaematis Rhizoma* (*Arisaema japonicum* BL.), 1–15 weight parts of *Gastrodiae Rhizoma* (*Gastrodia elata* BL.), 1–10 weight parts of *Acori Graminei Rhizoma* (*Acorus gramineus* Soland), 1–15 weight parts of *Ostericum Koreanum* or *Curcuma Longae Rhizoma* (*Curcuma longa* L.), 1–8 weight parts of *Caulis Phyllostachyos* or *Folium Phyllostachyos* (*Phyllostachys bambusoides* Sieb), 1–8 weight parts of *Bombycis Batryticatus* (*Bombyx mori* L.), 1–8 weight parts of *Fructus immaturus ponciri* (*Poncirus trifoliata* Raf), 2–20 weight parts of *Cyperi Rhizoma* (*Cyperus rotundus* L.), and 1–10 weight parts of *Saussurea Radix* (*Saussurea lappa* Clarke).

A preferred herbal composition of the present invention is extracted by the conventional method, where the extract comprises 10–50 weight parts of *Polygoni multiflori Radix*, 1–15 weight parts of *Gastrodiae Rhizoma*, 1–10 weight parts of *Acori Graminei Rhizoma*, 1–15 weight parts of *Ostericum Koreanum* or *Curcuma Longae Rhizoma*, 1–8 weight parts of *Caulis Phyllostachyos* or *Folium Phyllostachyos*, 1–8 weight parts of *Bombycis Batryticatus*, 1–8 weight parts of *Fructus immaturus ponciri*, 5–20 weight parts of *Poria*, 2–20 weight parts of *Aurantii nobilis Pericarpium*, 1–5 weight parts of *Glycyrrhizae Radix*, 1–10 weight parts of *Zingibreis Rhizoma*, and optionally 1–10 weight parts of *Pinelliae Tuber*.

Another preferred herbal composition of the present invention is also extracted by the conventional method, where the extract comprises 10–50 weight parts of *Polygoni multiflori Radix*, 1–10 weight part of *Polygalae Radix*, 1–10 weight parts of *Caryophylli Flos*, 1–10 weight parts of *Zingibreis Rhizoma*, 1–10 weight parts of *Arisaematis Rhizoma*, 1–10 weight parts of *Gastrodiae Rhizoma*, 1–8 weight parts of *Acori Graminei Rhizoma*, 1–10 weight parts of *Curcuma Longae Rhizoma*, 1–8 weight parts of *Folium Phyllostachyos*, 1–8 weight parts of *Bombycis Corpus*, 1–8 weight parts of *Fructus ponciri seu aurantii immaturus*, 5–20 weight parts of Poria, 1–10 weight parts of *Pinelliae Tuber*, 2–10 weight parts of *Aurantii nobilis Pericarpium*, and 1–5 weight parts of *Glycyrrhizae Radix*.

These extracts may be used as herbal medicines or supplementary drinks because they have shown excellent effects for the prevention and treatment of dementia. The herbal composition may be formulated as pellets, extract liquid preparations, granules, infused preparations, decocted preparations, tablets, capsules or parenteral preparations dissolved in distilled water, if deemed necessary, but the most preferably pellets.

One cannot ascertain the mechanism of each component of herbals to inhibit against AChE in their own nature but as a result of repeated comparative studies on some herbals having various composition, a herbal having the above herbal components and composition ratio has been confirmed to have the most optimal therapeutic efficacy.

According to the oriental medicinal theory, even if herbal drug compositions are similar, expected efficiencies and toxicities of each composition are quite different. Accordingly, the herbal composition of the present invention is comprised to enhance the therapeutic efficacy of the prevention and treatment of dementia and minimize the toxicity, thus providing the maximized effects.

The conventional herbal composition has recognized some disadvantage in that the excessive use of drug components has caused adverse reactions and toxicities, when clinical doses are administered. Since the use of ginseng, one of the active ingredients, is associated with some adverse reactions such as palpitation, blood-circulation disorder in patients with cardiovascular disease such as hypertension, and pulmonary tuberculosis, asthma and cough, the overall homeostatic imbalance in the body may easily occur. It is, therefore, preferred not to add ginseng to the composition of this invention. At this point it is quite difficult to screen some of novel active ingredients useful for the prevention and treatment of dementia, even though it is most preferred that the pharmacological action and clinical efficacy of the composition be sustained with little side effects. Therefore, the use of effective active ingredients in the composition represents the combination of entirely different components.

The present invention is characterized by the use of *Polygoni multiflori Radix* instead of ginseng used in the conventional arts, thus enhancing the pharmacological and clinical effectiveness for the prevention and treatment of dementia with reduced side effects.

*Polygoni multiflori Radix*, which is a main ingredient of the present invention, contains cresophanol, rein, emodin, physhion and their glycosides as active ingredients; it has been reported that these ingredients acting on intrinsic energy and blood of human are effective in promoting hepatic function, extra strength and blood nourishment. Unlike ginseng, *Polygoni multiflori Radix* has reportedly anti-aging properties such as better renal function, recovery of hair function and better body condition, as shown in several literatures (*Journal of Ethnopharmacology*, 75 (2001), 141–164). Specifically, *Polygoni multiflori Radix* is mainly indicated in the treatment of senile neurological disease and blood-circulation disorder such as cardiac pain, palsy and epilepsy. It is deemed that the adequate combination of *Polygoni multiflori Radix* with other herbal components may be effective in the prevention and treatment of dementia.

The present invention is embodied to maximize the anti-dementia effect and remove completely adverse reactions associated with using ginseng by replacing to *Polygoni multiflori Radix* as a main component based upon several conventional literatures and clinical rationale. *Polygoni multiflori Radix* itself has excellent hepatic enhancement and blood circulation, and synergy effect with other herbal components. However, excessive use of *Polygoni multiflori Radix* may adversely affect the cardio- and digestive systems; in case of using a small amount, the anti-dementia effect may not be expected.

The preferred components which can be used with *Polygoni multiflori Radix* are *Gastrodiae Rhizoma, Acori Graminei Rhizoma, Curcuma Longae Rhizoma, Folium Phyllostachyos, Bombycis Batryticatus, Fructus immaturus ponciri, Poria, Aurantii Nobilis Pericapium, Glycyrrhizae Radix, Zingiberis Rhizoma*, and optionally *Pinelliae Tuber.*

Further, a composition comprising *Polygoni multiflori Radix* as a main component, *Poria, Aurantii Nobilis Pericapium, Glycyrrhizae*, and *Pinelliae Tuber*, and optionally *Zingiberis Rhizoma* provides the effect expected from the present invention. The reason why the compositions of the present invention exhibit improved efficacy toward dementia without any adverse effects compared to the conventional herbal compositions is the use of *Polygoni multiflori Radix* as a main component.

Still further, when the composition of the present invention comprises *Polygoni multiflori Radix* as a main component, *Polygalae Radix, Caryophylli Flos, Arisaematis Rhizoma, Pinelliae Tuber*, and *Zingiberis Rhizoma*, it also exhibits superior effect toward dementia and reduced toxicities compared to the conventional herbal compositions due to the pharmacological synergy effect among the herbal medicines. Consequently, when *Polygoni multiflori Radix* is used as a main component in the herbal composition of the present invention, it is noted that the above-described compositions provide improvement in effectiveness toward dementia with little adverse reactions.

According to the present invention, the composition of the present invention may include *Caryophylli Flos*, known as a leading drug in the oriental field, together with *Polygoni multiflori Radix*. As a result, it has proven that the cerebral action has been further improved. In the aspect of pharmacology, the use of *Caryophylli Flos* may induce other active ingredients contained in the composition, resulting in better enhancement of cerebral action in terms of pharmacological and clinical action. However, if the amount of *Caryophylli Flos* is too low, it may reduce the anti-dementia effect but in case of using an excessive amount, vomiting and abdominal pain may occur.

Meantime, *Acorus Gramineicus* is indicated in the treatment of cerebral disorder such as dementia and amnesia. Since the use of *Acorus Gramineicus* itself in the conventional composition may not manifest sufficiently the anti-dementia effect, the inventor et al. has pursued another herbal component which can be mixed with *Acorus Gramineicus*. In consequence the inventor et al. has found out that the concurrent use of *Acorus Gramineicus* with *Polygalae Radix* exhibits the pharmacological synergy effect based upon the oriental theory of Chinese Pharmaceutics. With the addition of small amounts of *Polygalae Radix* with *Acorus Gramineicus*, the composition of this invention has successfully demonstrated better pharmacological action. However, the excessive use of Polygalae Radix with *Acorus Gramineicus* may be associated with blood-circulation disturbance and indigestion but in case of using a small amount of *Polygalae Radix* with *Acorus Gramineicus*, the anti-dementia effect may be reduced in the absence of any synergy effect with *Acorus Gramineicus*.

Further, the use of *Zingibreis Rhizoma* in the composition of this invention can alleviate various toxicities associated with such ingredients as *Pinelliae Tuber*, etc. In particular, *Pinelliae Tuber* comprises a lot of toxic alkaloids including ephedrine, its long-term or excessive use may produce blood-circulation disorder and neurological excitation. Thus the composition of this invention can maximize the anti-dementia effect through the removal of various toxicities using *Pinelliae Tuber*. However, a small amount of *Zingibreis Rhizoma* may cause any toxic effect but in case of excessive use of *Zingibreis Rhizoma*, the clinical efficacy in the composition of this invention may be decreased.

*Curcuma Longae Rhizoma* is preferred to *Ostericum Koreanum* due to its better compatibility with other components.

Especially, the appropriate use of various herbal components according to this invention can enhance the cerebral blood flow in the body, thus supplying sufficient amount of glucose to cerebral neurons as energy source to facilitate the glucose metabolism in the neurons.

The enhanced energy metabolism has contributed much to sustaining the homeostasis of cerebral neurons, while preventing the degeneration of cerebral neurons by inducing the secretion and separation of neurotransmitter.

Therefore, the pharmacological mechanism of this invention may be significantly effective in the prevention and treatment of dementia characterized by the gradual cognitive loss.

As described above, the anti-dementia composition of this invention contains *Polygoni multiflori Radix* as an active ingredient, as well as other herbal components such as *Polygalae Radix, Caryophylli Flos* and *Zingibreis Rhizoma*. With the various content ratios, the composition of this invention with better pharmacological effect and less adverse effects is quite effective in the prevention and treatment of dementia. In addition, the composition of this invention is an epoch-making anti-dementia drug and superior health food, when it is used for the general public during the long-term period.

It is noted that the significant pharmacological property of the herbal composition of the present invention results from the use of *Polygoni multiflori Radix* as an active ingredient and optimized content ratios of each ingredient. Appropriate compositions are embodied in various preparation examples and examples of this invention and the effectiveness of the composition in the prevention and treatment of dementia without adverse effects are proved through Experimental Examples.

Each component in the herbal composition of this invention is extracted from water or alcohol. For example, said mixture is extracted with water after heating for 4–10 hrs or with ethanol for 2–5 hrs, filtered, and evaporated to give a powder which is further formulated by adding additives to obtain one of appropriated preparations.

When the herbal composition of this invention is orally administered as pellets for the desired therapeutic effect to patients who suffer from senile dementia, an extract powder for an adult (60 kg) may be administered 2–4 times daily with a dose of 5–15 g, preferably 7.5–12.5 g each time.

The administration dose has been determined with consideration of toxicities and adverse effects. When the excess amount of the herbal composition is administered for long term, it has not shown severe side effects and provided superior therapeutic effects to small administration.

When the herbal extracts having ginseng as an effective component is administered to patients, it requires special care because most of patients are suffering from hypertension. However, the herbal composition of this invention can be safely administered to patients suffering from hypertension, other blood-circulation disorder or hepatic disease with much less side effects and thus, it is highly expected to be used as functional health food.

Since the conventional herbal compositions having anti-dementia effect have not been standardized or merchandized to be used widely, it has been limited to a single-medicine prescription or localized treatment with a high price. However, the herbal composition of the present invention is standardized for effective combinations and taken simply by general publics to prevent or cure dementia.

Further, the herbal composition of the present invention is effective in improving one's memory or having a clear head. For this purpose, does may be lowered to 30–70% compared to that for the treatment of dementia.

The construction and effect of the invention is explained in detail based on the following manufacturing examples and experimental examples as set forth hereunder. However, these examples and experimental examples are the ones to further understand this invention and thus, the scope of this invention is not limited by these examples and experimental examples in any respects.

Especially, Experimental Examples 1–11 of the present invention compare the effectiveness of the compositions of Example 1 and Comparative Example 1, which is Example 1 of the U.S. Pat. No. 6,010,702. On the purpose of direct comparison, Experimental Examples 1–11 of the present invention were performed same as Experimental Examples in the U.S. Pat. No. 6,010,702.

EXAMPLE 1

Medical herbs were purchased from the Korea Medicinal Herb Association and authenticated by botanists at College of Oriental Medicine, Wonkwang University. A composition of Example 1 was prepared from the combination of 15 medicinal herbs as follows: *Polygoni multiflori Radix* (20 g), *Polygalae Radix* (3 g), *Caryophylli Flos* (1 g), *Arisaematis Rhizoma* (7 g), *Gastrodiae Rhizoma* (8 g), *Acori Graminei Rhizoma* (4 g), *Ostericum Koreanum* (8 g), *Caulis Phyllostachyos* (3 g), *Bombycis Corpus* (3 g), *Fructus ponciri seu aurantii immaturus* (3 g), *Poria* (8 g), *Pinelliae Tuber* (8 g), *Aurantii nobilis Pericarpium* (7 g), *Glycyrrhizae Radix* (2 g), and *Zingibreis Rhizoma* (4 g). The mixture was placed in 0.8 L of water, heated slowly and refluxed for 4–10 hrs. Then, a liquid-phase solution was filtered through filter paper and filtrate was dried over freeze dryer to obtain a light-brown powder (10.0 g).

EXAMPLES 2–7

A powder composition prepared from the combination of 15 medicinal herbs was prepared to have the following component ratios shown in Table 1.

TABLE 1

| Component | Used amount (g) | | | | | | |
|---|---|---|---|---|---|---|---|
| | Ex. 1 | Ex. 2 | Ex. 3 | Ex. 4 | Ex. 5 | Ex. 6 | Ex. 7 |
| *Polygoni multiflori Radix* | 20 | 15 | 18 | 20 | 20 | 30 | 30 |
| *Polygalae Radix* | 3 | 4 | 2 | 5 | 4 | 4 | 3 |
| *Caryophylli Flos* | 1 | 1.5 | 2 | 3 | 3 | 1 | 1 |
| *Arisaematis Rhizoma* | 7 | 8 | 5 | 10 | 8 | 8 | 8 |
| *Gastrodiae Rhizoma* | 8 | 7 | 8 | 8 | 8 | 8 | 8 |
| *Acori Graminei Rhizoma* | 4 | 4 | 3 | 3 | 3 | 2 | 3 |
| *Ostericum Koreanum* | 8 | 4 | 8 | 8 | 10 | 10 | 5 |
| *Bambusae Caulis In Taeniam* | 3 | 4 | 4 | 4 | 3 | 3 | 3 |
| *Bombycis Corpus* | 3 | 4 | 4 | 4 | 3 | 3 | 2 |
| *Fructus ponciri seu aurantii immaturus* | 3 | 4 | 4 | 4 | 3 | 3 | 2 |
| *Poria* | 8 | 7 | 8 | 8 | 10 | 10 | 10 |
| *Pinelliae Tuber* | 8 | 7 | 10 | 10 | 8 | 8 | 8 |
| *Aurantii nobilis Pericarpium* | 7 | 8 | 10 | 10 | 10 | 8 | 8 |
| *Glycyrrhizae Radix* | 2 | 2 | 2 | 2 | 2 | 2 | 2 |
| *Zingibreis Rhizoma* | 4 | 10 | 2 | 8 | 8 | 5 | 10 |
| Water | 0.8 L | 1 L | 0.8 L | 1.5 L | — | — | — |
| Ethanol | — | — | — | — | 0.8 L | 1.5 L | 1.5 L |
| Yield | 10.0 | 9.9 | 10.2 | 12.0 | 10.8 | 12.5 | 13.0 |

EXAMPLES 8–10

Compositions of Examples 8–10 were prepared from the combination of 15 medicinal herbs with the contents listed in Table 2.

An extract of the prescription was prepared by decocting the mixed herbs with 10 times (v/w) of $H_2O$ for 2 hrs. After filtration, the residues were boiled for additional 2 hrs. Filtrates were mixed together, and lyophilized by freeze drier (Labconco, Preezone). Extracts were kept at 4° C. until use. The yield of extract was ≈16% of dried ingredient weight. All voucher specimens (HM2001-45) are deposited in the herbarium of the Department of Pharmacology, Wonkwang University School of Medicine. The chemical constituents of crude extract were analyzed by thin layer chromatography.

TABLE 2

| Component | Used amount (g) | | |
|---|---|---|---|
| | Ex. 8 | Ex. 9 | Ex. 10 |
| *Polygoni multiflori Radix* | 27.2 | 30 | 16 |
| *Polygalae Radix* | — | — | 2 |
| *Caryophylli Flos* | — | — | 1.2 |
| *Arisaematis Rhizoma* | — | — | 8 |
| *Gastrodiae Rhizoma* | 8 | 7 | 8 |
| *Acori Graminei Rhizoma* | 4 | 4 | 4 |
| *Curcuma Longae Rhizoma* | 8 | 6 | 8 |
| *Caulis Phyllostachyos* | 4 | 4 | 4 |
| *Bombycis corpus* | 4 | 4 | 4 |
| *Fructus ponciri seu aurantii immaturus* | 4 | 4 | 4 |
| *Poria* | 12 | 8 | 8 |
| *Pinelliae Tuber* | — | 7 | 8 |
| *Aurantii nobilis Pericarpium* | 12 | 8 | 8 |
| *Glycyrrhizae Radix* | 2 | 2 | 2 |
| *Zingibreis Rhizoma* | 4 | 4 | 4 |

Comparative Example 1

A mixture consisting of ginseng (50 g), *Arisaematis Rhizoma* (15 g), *Gastrodiae Rhizoma* (15 g), *Acori Graminei Rhizoma* (10 g), *Ostericum Koreanum* (10 g), *Barnbusae Caulis In Taeniam* (10 g), *Bombycis Corpus* (10 g), *Fructus ponciri seu aurantii immaturus* (10 g), *Poria* (10 g), *Pinelliae Tuber* (10 g) and *Aurantii nobilis Pericarpium* (6 g) and *Glycyrrhizae Radix* (6 g) was placed in 1 L of water, heated slowly and refluxed for 6–8 hrs. Then, a liquid-phase solution was filtered through a filter paper and filtrate was completely dried over a freeze dryer to obtain a brown powder (12.2 g).

Comparative Example 2

A herbal mixture containing the same components and composition ratio as Example 1 was extracted 1 L of ethanol for 3 hrs. Then, a liquid-phase solution was filtered through a filter paper and filtrate was completely dried over a freeze dryer to obtain a brown powder (14.1 g).

Experimental Example 1

Inhibitory Activity Against AChE

To evaluate the inhibitory effect of an extract of this invention on AChE, each extract powder (0.025, 0.05 and 0.1 mg/ml) prepared from Example 1 was added to an enzyme (1,000 units) extracted from an electric eel (AChE: Sigma Cat. No. C-2888) dissolved in 1 ml PBS (phosphate buffer: 0.1M, pH 7.4). Based on a each AChE activity was measured by Ellman's coupled assay using an UV-visible spectrophotometer at 412 nm using a velocity constant factors of enzyme, Km (Micaelis constant), Vmax (maximum speed) and 5,5-dithio-bis-(2-nitrobenzoic acid: DTNB) as a coupling agent. As shown in the following table 3, the inhibitory effect of an extract of this invention on AChE showed that at doses of 0.05 mg/ml and 0.1 mg/ml, the extract of this invention induced decrease in the enzymatic activity by 30.3% and 80.4%, respectively.

TABLE 3

| Amount of herbal | Loss of enzymatic activity (%) | |
|---|---|---|
| (mg/ml) | Example 1 | Comparative Example 1 |
| 0 | 0 | 0 |
| 0.025 | 15.2 | 13.6 |
| 0.05 | 30.3 | 21.0 |
| 0.1 | 80.4 | 59.8 |

It can be safely said that the inhibitory activity (80.4%) of the herbal extract of this invention on AChE is quite remarkable, in consideration of the fact that THA (brandname: Cognex) exhibits about an inhibitory action on AChE by 40% at maximum (ref: Keio J. Med., 36, 381, 1987), and the conventional extracts of U.S. Pat. No. 6,010,702 exhibits 59.8% (Comparative Example 1).

Experimental Example 2

Inhibitory Activity Against AChE

Through in vivo study to evaluate the inhibitory effect of an extract of this invention on AChE, 20-week-old rats were divided into 2 groups (experimental and control groups) consisting of 7 individuals each prior to commencement of administration. A solution containing 0.5 g of powder, so prepared from Example 1, dissolved in 100 ml distilled water was orally administered to the treatment group at a daily dose of 3 ml for consecutive days, while no medication was given to the control group. After 10 days, the brain of rats was removed to weigh the total weight of brain. Then, 5 ml PBS (0.1M, pH 7.4) was added to the brain, crushed completely, and stirred slowly for 3–5 hrs. 2 ml PBS (0.1M, pH 7.4) was further added to the solution of brain cell for stirring, centrifuged (Hettich Rotina 48R) at 1,000 rpm at 4□ for 10 minutes centrifuge and purified by a filter (CAMEO 25ES nitrocellulose pore size: 0.45 mm)

The AChE activity of rat brain was measured by Ellman's coupled assay (Ellman, G. L., *Biochem. Pharmacol.*, 7, 88, 1961) using an UV-visible spectrophotometer at 412 nm. Hence, the enzymatic reaction rate on all substrates at the intervals of time was calculated by Michaelis-Menten equation. The purified brain was incubated in a 1 ml quartz cuvette containing 790 ul of PBS (0.1M, pH 7.3), 60 µl substrate in 5 ml solution (ATcH: acethylthiocoline) and 120 µl DTNB (dithionitrobenzoic acid) in 5 mM solution as a coupling agent for about 3 minutes and then, each 10 ul of brain solution extracted from the treatment and control groups was added to the quartz cuvette for assessment of AChE activity, as shown in the following table 4.

TABLE 4

| Classification | Mean initial rate of AChE (AU/s) | Loss of AChE activity (%) |
|---|---|---|
| Normal rats | $3.100 \times 10^{-3}$ | 0 |
| Rats with oral administration of herbal extract of Comp. Ex. 1 (3 ml/day) | $2.384 \times 10^{-3}$ | 23.1 |
| Rats with oral administration of herbal extract of Ex. 1 (3 ml/day) | $2.042 \times 10^{-3}$ | 34.1 |

From the above in vivo test, it was noted that when the herbal extract of this invention was administered to rats for 10 consecutive days, the AChE activity was reduced by 34.1% compared with rats having no medication. This is much more improved than the activity (23.1%) of Comparative Example 1. Thus, it has proven that the herbal extract of this invention has an improved inhibitory action on AChE.

Experimental Example 3

Comparison of Neurontransmitter Acetylcholine Concentration

Female Sprague-Dawley rats (pyrogen test free) at three weeks of age were purchased and housed at 23–25□ in a light/dark cycle to grow 20-week-old rats (250–350 g) for use in this study. The herbal extract prepared from Example 3 of this invention was orally administered to each experimental rats consisting of 7 individuals for 10 days in the same manner as Experimental Example 2. After 5 and 10 days of administration, all rats were necropsied and the weight of brain was measured. The brain cells were homogenized by 10 ml PBS (phosphate buffer: 0.1M, pH 7.4) containing 0.2% tripton X-100 and centrifuged (1,000 rpm) at 4° C. to isolate acetylcholine from the brain cell solution. The acetylcholine, so isolated, was assayed by HPLC equipped with an electrode detector. Some standard graphs of acetylcholine at accurate concentrations were prepared to analyze each sample of 20 µl extracted from the rat brain under the same conditions (flow rate: 10 ml/min, detection scope: 3,9062 nA, solvent: 0.1M PBS at pH 7.4). When each group consisting of 7 rats was given an herbal extract to their brains at the intervals of time to compare their level of acetylcholine, so biochemically isolated, with that of normal rats, the results were shown in the following table 5.

TABLE 5

| Day | Amount of acetylcholine (µM) | Increasing rate of acetylcholine (%) | No. of rats |
|---|---|---|---|
| 0 (normal rats) | 107.7 | 0 | 7 |
| 5 (Comp. Ex. 1) | 165.1 (139.6) | 53.3 (29.6) | 7 |
| 10 (Comp. Ex. 1) | 241.2 (193.4) | 123.9 (79.6) | 7 |

The above results indicated that the actual concentration of neurontransmitter acetylcholine was increased in rats with the herbal extract of this invention, thus reflecting the actual inhibitory effect of such herbal extract on AChE in the body. The concentration of acetylcholine was increased by 53.3% and 123.9% after 5-day and 10-day administration of the herbal extract, respectively. The herbal extract of this invention has more 5-fold potent inhibitory action on AChE than the composition disclosed in the Japanese Patent Publication No. 7-25760, and 2-fold than the composition of Comparative Example 1, while having at least 4-fold potent inhibitory action on AChE than synthetic anti-dementia agents for the prevention and treatment of dementia (Keio J. Med., 36, 381, 1987). In particular, the naturally occurring herbals used for this studies, which have been clinically used for several thousand years as other purposes of use, has little adverse reactions which have encountered in the medication using the conventional drugs (ref: Experimental Example 11).

Experimental Example 4

Pellets and Its Efficacy Screening 1 g of a dried pellet form prepared from the mixing of 5 g of honey with 100 g of herbal powder, so prepared from Example 4, was dissolved in water (10 ml) every day for its oral administration to 20-week-old Sprague-Dawley rats for 10 consecutive days. After 10 days, the activity of AChE and acetylcholine level in brain was measured in the same manner as Experimental Examples 2 and 3. The results of this experiment revealed that the pellet form had the same inhibitory activity against AChE with increasing concentration of acetylcholine, as in Experimental Examples 2 and 3.

Experimental Example 5

Powders and Its Efficacy Screening 100 g of herbal powder, so prepared from Example 5, was finely pulverized, passed through No. 18 sieve (850 µg), followed by the addition of lactose (200 g) as a diluent to prepare a powder form. Each 0.7 g of the powder form was dissolved in water (10 ml) every day for its oral administration to 20-week-old Spague-Dawley rats for 10 consecutive days. After 10 days, the activity of AChE and acetylcholine level in brain was measured in the same manner as Experimental Examples 2 and 3. The results of this experiment revealed that the powder form had the same inhibitory action on AChE with increasing concentration of acetylcholine, as in Experimental Examples 2 and 3.

Experimental Example 6

Tablets and Its Efficacy Screening 100 g of herbal powder, so prepared from Example 6, was mixed with 25 g of lactose and 5 g of starch and with the addition of talc (5 g), the mixture was formulated by a tabletting machine to prepare a film-coated tablet. Each 0.7 g of the tablet form was dissolved in water (10 ml) every day for its oral administration to 20-week-old Sprague-Dawley rats for 10 consecutive days. After 10 days, the activity of AChE and acetylcholine level in brain was measured in the same manner as Experimental Examples 2 and 3. The results of this experiment revealed that the tablet form had the same inhibitory action on AChE with increasing concentration of acetylcholine, as in Experimental Examples 2 and 3.

Experimental Example 7

Granules and Its Efficacy Screening 100 g of herbal powder, so prepared from Example 7, was mixed with 25 g of lactose and 5 g of starch, passed through a sieve (No. 12-45) to prepare a granule form. 1.0 g the granule form was dissolved in water (10 ml) every day for its oral administration to 20-week-old Sprague-Dawley rats for 10 consecutive days. After 10 days, the activity of AChE and acetylcholine level in brain was measured in the same manner as Experimental Examples 2 and 3. The results of this experiment revealed that the granule form had the same inhibitory action on AChE with increasing concentration of acetylcholine, as in Experimental Examples 2 and 3.

Experimental Example 8

Capsules and Its Efficacy Screening 100 g of herbal powder, so prepared from Example 1, was filled into a capsule (No. 3, 0.3 ml). Each 0.7 g of the capsule form was dissolved in water (10 ml) every day for its oral administration to 20-week-old Sprague-Dawley rats for 10 consecutive days. After 10 days, the activity of AChE and acetylcholine level in brain was measured in the same manner as Experimental Examples 2 and 3. The results of this experiment revealed that the capsule form had the same inhibitory action on AChE with increasing concentration of acetylcholine, as in Experimental Examples 2 and 3.

Experimental Example 9

Infused Preparations and Its Efficacy Screening

A herbal mixture having the same components and composition ratio as Example 1 was finely pulverized and with the addition of purified water (200 ml), precipitated for 3 hrs. A thermally-purified water (700 ml) was added and mixed to the resulting solution several times, cooled and filtered by a cotton. 50 g of honey as a cordial was further added to the solution. Each 3 ml of the percolated preparations was orally administered to 20-week-old Sprague-Dawley rats for 10 consecutive days. After 10 days, the activity of AChE and acetylcholine level in brain was measured in the same manner as Experimental Examples 2 and 3. The results of this experiment revealed that the percolated preparations had the same inhibitory action on AChE with increasing concentration of acetylcholine, as in Experimental Examples 2 and 3.

Experimental Example 10

Decocted Preparations and Its Efficacy Screening

Purified water (900 ml) was added and mixed several times to a herbal mixture having the same components and composition ratio as Example 1, heated for more than 30 min and filtered off in warm state. 50 g of honey were added to the resulting solution as a flavoring agent. Each 3 ml of the boiled agent was orally administered to 20-week-old Sprague-Dawley rats for 10 consecutive days. After 10 days, the activity of AChE and acetylcholine level in brain was measured in the same manner as Experimental Examples 2 and 3. The results of this experiment revealed that the percolated preparations had the same inhibitory action on AChE with increasing concentration of acetylcholine, as in Experimental Examples 2 and 3.

Experimental Example 11

Liver Function Test of Rats in Serum 20-week-old Sprague-Dawley rats were divided into a placebo group (8 rats) and a Experimental group (9 rats). 500 mg of herbal powder, so prepared from Example 1, was dissolved in purified water (100 ml) and then, each 3 ml of the solution was orally administered to the treatment group at 10 o'clock every morning for 10 consecutive days. After 10 days, the animals were sacrificed to collect the blood samples. The blood samples were centrifuged at 1500 rpm at 4° C. for 10 min to separate the sera. Then, the liver function test on such sera was performed according to the conventional method. As revealed in the following table 6, it was noted that both groups had nearly similar levels in AST, ALT, ALP and BUN, thus reflecting that the herbal of this invention had no primary hepatotoxicity. Especially, the herbal extract of this invention showed much lower hepatotoxicity than that of control group which is Comparative Example 1.

TABLE 6

Concentration of various parameters in blood

| Group | AST (IU/l) | ALT (IU/l) | ALP (IU/l) | BUN (IU/l) | n |
|---|---|---|---|---|---|
| Placebo | 171.3 ± 26.6 | 56.4 ± 14.8 | 433.3 ± 181.3 | 21.2 ± 3.0 | 8 |
| Experimental | 135.1 ± 28.2 | 56.8 ± 11.4 | 430.1 ± 89.3 | 21.5 ± 1.9 | 9 |
| Control | 112.2 ± 38.1 | 58.1 ± 14.8 | 421.3 ± 101.1 | 22.3 ± 2.3 | 9 |

Experimental Example 12

Ovariectomy Test

The herbal composition, namely Neuroclean (NC), was prepared by modification of the traditional prescriptions which have been used as a remedy for cerebroneuronal diseases, and investigated for the effects on the cerebral adenosine triphosphate (ATP) and acetylcholine (ACh) contents in ovariectomized (OVX) rats. Female Sprague-Dawley rats were ovariectomized, and maintained for 12 weeks to deplete ovarian steroid hormones, followed by oral administration of NC at 500 mg/kg body weight per day for 14 weeks. The administration of NC markedly attenuated the high rate of body weight increase in OVX rats, and also reduced the decline of cerebral weight caused by ovariectomy ($p<0.05$). Superfusion of NC at 50 mg/kg body weight significantly increased the rate of cerebral blood flow, but not changed the mean arterial blood pressure. Deprivation of ovarian steroid hormones significantly decreased the cerebral ATP, choline and ACh contents, and such reductions were completely restored by treatment of OVX rats with NC ($p<0.01$). Additionally, NC also significantly elevated the cerebral choline acetyltransferase activities declined by OVX ($p<0.01$). Taken together, these results suggest that pharmacological properties of NC may be implicated in the improvement of synthetic pathways of cerebral energy and cholinergic neurotransmitter declined by deprivation of ovarian steroid hormones, and NC may be a promising herbal remedy for treatment of cerebroneuronal dysfunctions including dementia.

Although many factors are attributed to the cause of Alzheimer's disease (AD), a consistent finding is a depressed central cholinergic system, characterized by decreased presynaptic cholinergic markers such as acetylcholine (ACh) and choline acetyltransferase (ChAT, Coyle et al 1983: Soininen et al 1995). This association and the production of memory impairments induced from cholinergic hypofunction have prompted considerable interest in cholinergic replacement therapy. Additionally, it is also believed that decline of glucose metabolism to produce cerebroneuronal energy, adenosine triphosphate (ATP), appears to induce a cascade of disturbances that leads to abnormal amyloid formation, membrane damages, neuronal degeneration and cognitive impairments in Alzheimer patients (Hoyer 1996: Meier-Ruge et al 1994). The retrospective studies suggested that ovarian steroid hormones were especially relevant to memory and cognitive functions of cerebral neurons, and their deprivations might be implicated in the incidence of neurodegenerative diseases including AD (McEwen et al 1997: Paganini-Hill and Henderson 1994). In animal studies, deprivation of ovarian steroid hormones by ovariectomy (OVX) causes a decrease in high affinity choline uptake in the hippocampus and frontal cerebral cortex of rats (O'Malley et al 1987), and leads to disruption in learning and memory functions (Singh et al 1994: Toriizuka et al 2000). Therefore, it is widely believed that deficit of cerebral ATP and choline contents may be associated with development of progressive neurodegeneration characterized by learning and memory impairments.

On the other hand, there are a variety of traditional formulae remedies that have been often used as a prescription for diseases associated with disturbances of cerebrovascular system in Hanbang (Korean traditional herbal medicine). The pharmacological concepts of these remedies are that they enhance cerebral blood circulation through removing biologically harmful substances, which may be accumulated in the peripheral vascular systems. Regarding in their pharmacological properties, we newly constituted a novel herbal medicine, Neuroclean (NC), which may be useful for prevention and/or treatment of cerebroneuronal dysfunctions caused by disturbance of cerebral blood flow (CBF). We hypothesized that NC might enhance the cerebroneuronal blood circulation declined by a variety of pathological causes, and the increased cerebral blood circulation might improve the metabolism of cerebroneuronal glucose and cholinergic pathways, resulted in elevated cerebral ATP and ACh contents. In order to clarify this hypothesis, the present study investigated the pharmacological properties of NC on the changes of cerebroneuronal ATP and ACh contents in OVX rats.

[Animal Treatment and Tissue Preparation]

Female Sprague-Dawley rats were obtained from Korea Experimental Animal Center (Cheonan, Korea) at 6-week old, and used after 1 week of preliminary breeding under 12 hrs light and dark cycle at 24–26° C. They were allowed free access to a commercial rodent diet (Samyang, Korea) and tap water during experimental period. Both ovaries of the experimental animals were removed under pentobarbital sodium (Nembutal, 50 mg/kg body weight) anesthesia at 7-week old, and maintained for 12 weeks to deplete ovarian steroid hormones. Sham operations were done for the control rats. NC extracts dissolved in $H_2O$ were orally administered at 500 mg/kg body weight per day for 14 weeks. Control animals were orally received an equal volume of water instead of herbal medicine. Administration volume was adjusted to 2 ml/kg body weight. At 14 weeks after starting experiment, all animals were anesthetized with ethyl ether and sacrificed. The brain was removed immediately after blood sample was collected from abdominal vein and washed with ice-cold phosphate-buffered saline (PBS, pH 7.4), followed by measurement of cerebral weight. The cerebral cortex was dissected as soon as possible onto ice, and kept at –80° C. until use.

[Monitoring of Cerebral Blood Flow]

Measurements of CBF were carried out according to the methods of Dimagl et al. (1989) with a slight modification. Briefly, male Sprague-Dawley rats (200–250 g) were anesthetized with halothane, and trachea was intubated. One of the femoral arteries was cannulated for recording of mean arterial blood pressure (MABP), and the other femoral vein was cannulated for infusion of herbal extracts. A small craniotomy (2×2 mm) was performed to expose the parietal cortex, the dura was removed, and the site was superfused with Ringer solution (37° C., pH 7.4). CBF was continuously monitored at the site of superfusion with a laser-Doppler probe (Vasamedic, St. Paul, Minn.) positioned stereotaxically on the cortical surface. CBF values were expressed as a percentage increase relative to the resting level. Zero values for CBF were obtained after the heart was stopped by an overdose of halothane at the end of the experiment. Although laser-Doppler flowmetry is not quantitative, it monitors relative changes in CBF quite accurately (Dirnagl et al 1989).

[Measurement of Cerebral ATP Contents]

By using the microchemiluminescent method described in our previous report (Ma et al 2000), intracellular ATP contents of frontoparietal cerebral cortex were measured. In all protocols, there were at least duplicate measurements of intracellular ATP content for any given rats. Cerebral ATP was extracted by adding 500 µl of 10% trichloroacetic acid (TCA)/1 mM EDTA to 0.1 g tissue weight and homogenized. To complete the extraction, samples were vibrated for 2 min by a vortex mixer (Thermolyne 37600). The solution containing denatured tissues were briefly centrifuged at 4° C., and 10 µl of supernatants were transferred to polystyrene cuvettes (BioOrbit, Sweden) filled with 390 µl of Tris/acetate buffer (pH 7.75) containing 0.5 mM EDTA. Cuvettes were placed in a luminometer (BioOrbit 1251). After adding 100 µl of ATP monitoring reagents by auto-dispenser, the light intensity was automatically measured for 10 sec by a computer-driven system. Production of light intensity was a linear fashion for $10^{-14}$ to $10^{-11}$ mol of ATP per tube in our assay system.

[Measurement of Cerebral Choline Contents]

Intracellular choline contents of frontoparietal cerebral cortex were measured by chemiluminescent method described in detail in our previous report (Ma et al 2000). In brief, cerebral cortexes (0.1 g) were homogenized with a glass-Teflon pestle in 10 times (v/w) of 7% perchloric acid, and centrifuged at 3,000 rpm (Beckman, Avanti 30) for 10 min. Supernatants were then neutralized with 2M $K_2CO_3$, and potassium-perchlorate precipitates were removed by a brief centrifugation. A total of 20 µl of diluted samples plus 380 µl of glycine buffer (pH 8.6) were analyzed for choline in a luminometer (BioOrbit 1251) by adding automatically 100 µl of reagents. The reagents were freshly prepared each day for use, and contained 1 ml of 2 mg/ml horse radish microperoxidase, 60 µl of 10 mM luminol and 50 U of choline oxidase in the glycine buffer (pH 8.6). The integrity of light production between 5 and 25 sec after adding reagents was linear with choline content between 1 pmol and 100 nmol per tube in this system. There were at least duplicate measurements of cellular choline contents for any given rats.

[Cerebral Choline Acetyltransferase Activity]

Choline acetyltransferase (ChAT) activities of frontoparietal cerebral cortex were measured according to the method described by Fonnum (1975) with slight modification. In brief, cerebral cortexes (100 mg) were homogenized by use of a sonicator in 10 mM EDTA containing 0.2% Triton X-100, and centrifuged at 1,000 g (Beckman, Avanti 30) for 10 min. The supernatants were incubated in a final volume of 300 µl of a mixture containing NaCl (300 mM), phosphate buffer (40 mM, pH 7.4), eserine sulfate (0.1 mM), EDTA (10 mM), choline chloride (10 mM), [$^3$H]acetyl-coenzyme A (100 nCi, 0.2 mM) and Triton X-100 (0.05%). Mixtures were incubated at 37° C. for 15 min. At the end of the incubation period, the incubation media were diluted with 2.5 ml of 10 mM sodium phosphate buffer (pH 7.4), and 3 ml of acetonitrile containing 15 mg of sodium tetraphenylborate and 10 ml of toluene were added for the extraction of ACh. Both labeled and unlabeled ACh were partitioned into the toluene phase, whereas unreacted substrate remained in the aqueous phase. Radioactivity was measured by a Beckman (LS 6500) scintillation counter.

[Measurement of Cerebral Acetylcholine Contents]

ACh contents of frontoparietal cerebral cortex were measured by chemiluminescent method described in detail in the previous report (Israel and Lesbats 1982). Briefly, The extraction and oxidation of tissue samples were performed as follows: Cerebral cortexes (100 mg) were extracted with 1 ml of 5% TCA, and TCA was removed by ether washing, followed by centrifugation at 1,000 g for 10 min. After allowing the residual ether to evaporate, the aqueous phase was neutralized and buffered. The samples (100 µl) were oxidized by adding 10 µl of 0.5% sodium metaperiodate. The oxidized sample (50 µl) and reaction mixture containing 10 ml of 0.2M sodium phosphate buffer (pH 8.6), 100 µl of choline oxidase (250 U/ml), 50 µl of horse radish peroxidase (type II, 2 mg/ml) and 100 µl of luminol (1 mM) were mixed together. Subsequently, 5 µl of acetylcholinesterase (1,000 U/ml) was added to trigger the hydrolysis of ACh, and light emission was measured with a luminometer (BioOrbit 1251). Protein was determined according to the method of Lowry et al. (1951).

[Reagents]

Choline oxidase, microperoxidase, luminol, ATP and choline chloride were obtained from Sigma (St. Louis, Mo., USA). ATP monitoring reagent and [acetyl-$^3$H]acetyl-coenzyme A (1.6 Ci/mmol) were purchased from BioOrbit (Sweden) and NEN Dupont (Boston, Mass., USA), respectively. All other chemicals were of the highest grade from commercial sources.

[Statistical Analysis]

Values obtained in this study were expressed as mean±S.E. Statistical significance was performed by ANOVA and Student's t-test, and differences were considered to be significant at $p<0.05$.

Results

[Changes of Body Weight and Cerebral Weight]

As shown in FIG. 1, body weight of OVX rats was highly increased throughout the period of this study compared to that of sham animals, and a significant difference of body weight between sham and OVX rats was observed at 26 weeks after ovariectomy ($p<0.01$). Increases in rate of body weight in OVX rats were substantially reduced by oral administration of NC at 500 mg/kg body weight per day for 14 weeks. Oral administration of NC significantly reduced the increased rate of body weight in OVX rats ($p<0.05$), but not in sham rats. Interestingly, it was noted that treatment of OVX rats with NC conspicuously improved behavioral activity and body-surface features, such as coat condition, in OVX rats.

Figure 2:
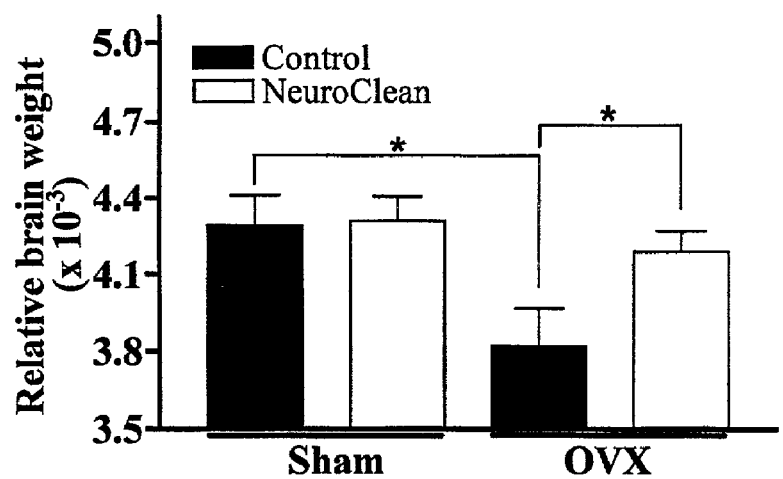
FIG. 2 represents effects of Neuroclean on the relative cerebral weights in sham and OVX rats, where results were expressed as mean±S.E. of 10 rats (*p<0.05)

FIG. 2 shows the changes of cerebral weight in sham and OVX rats treated with and without NC. The relative cerebral weight to body weight in OVX rats was significantly lower compared to that in sham rats ($p<0.05$). This decrease was partially recovered by treatment of OVX rats with NC for 14 weeks ($p<0.05$). In contrast, NC did not affect the relative cerebral weight to body weight in sham rats.

[Cerebral Blood Flow]

Figure 3:
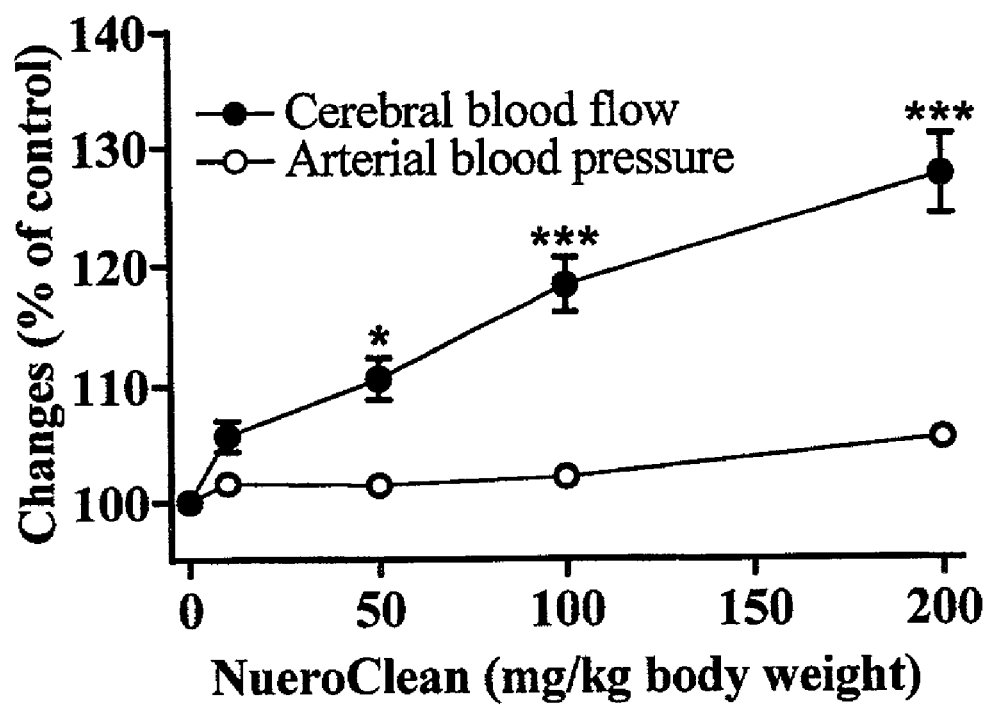
FIG. 3 represents effects of Neuroclean on cerebral blood flow and mean arterial blood pressure, where results were expressed as mean±S.E. of 7 rats (*p<0.05, **p<0.01)

This study measured the effects of NC on CBF and MABP by using laser-Doppler system and electric microtransducer, and results are shown in FIG. 3. CBF was stable during superfusion with normal Ringer. Superfusion with NC (10–200 mg/kg body weights) increased resting CBF in a dose-dependent manner. Increasing at 50, 100, 200 mg/kg averaged 110.5±1.74%, 118.3±2.28% and 127.6±3.35% of resting CBF, respectively. These increases were significantly different from the value of resting CBF ($p<0.05$–0.01). Although NC only at concentration of 200 mg/kg body weight slightly increased the MABP (105.4±0.03% of resting value), all doses tested in this study did not significantly change the MABP.

[Cerebral ATP and Chloine Contents]

Figure 4:
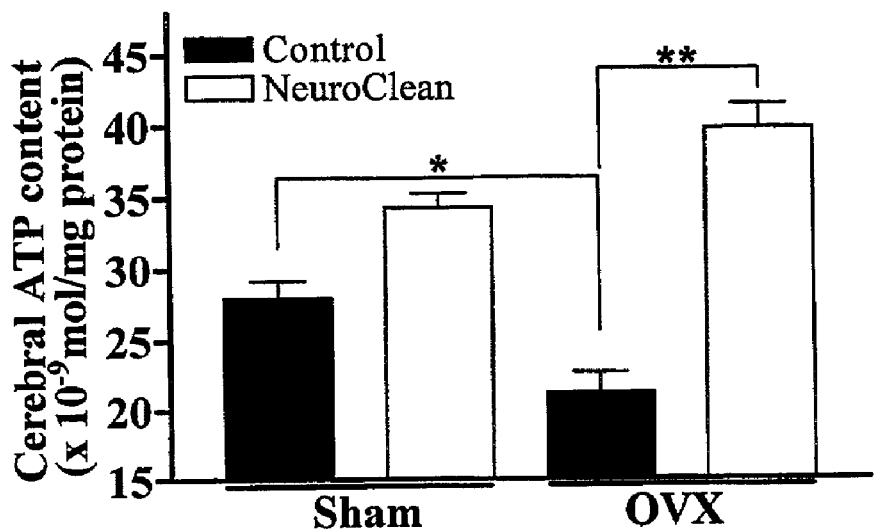
FIG. 4 represents increases of cerebral ATP contents by Neuroclean in OVX rats, where results were expressed as mean±S.E. of 10 rats (*p<0.05, **p<0.01)

This study measured intracellular ATP contents of frontoparietal cerebral cortex in sham and OVX rats, and results are shown in FIG. 4. At 26 weeks after ovariectomy, cerebral ATP contents (21.2±1.45×10$^{-9}$ mol/mg protein) in OVX rats were significantly low compared to these (27.9±1.24) in sham animals ($p<0.05$). Oral administration of NC completely restored the cerebral ATP contents decreased by deprivation of ovarian steroid hormones in OVX rats, but not in sham rats.

Figure 5:
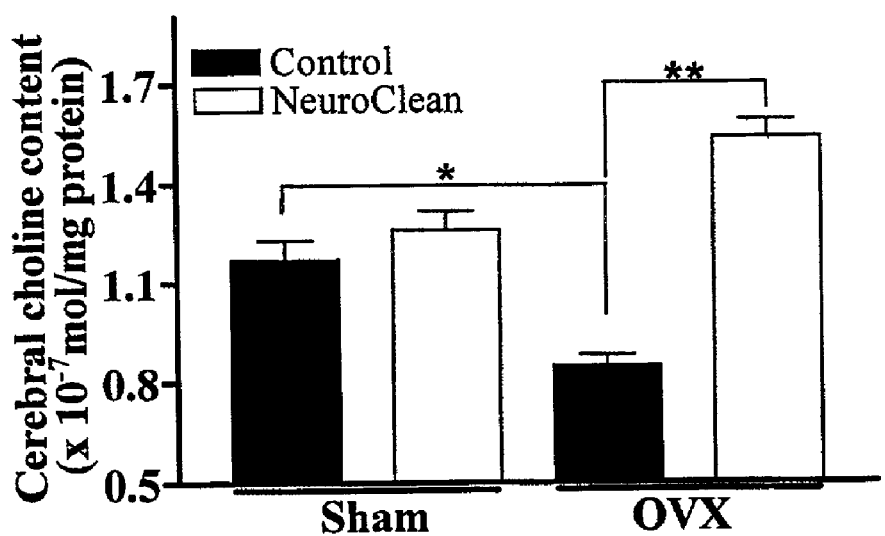
FIG. 5 represents increases of cerebral choline contents by Neuroclean in OVX rats, where results were expressed as mean±S.E. of 10 rats (*p<0.05, **p<0.01)

As shown in FIG. 5, choline contents (1.17±0.058×10$^{-7}$ mol/mg protein) of frontoparietal cerebral cortex in sham rats were dramatically lowered by deprivation of ovarian steroid hormones for 26 weeks. The reduction of cerebral choline contents (0.85±0.034) in OVX rats were significantly restored by NC administration for the last 14 weeks ($p<0.01$). However, NC administration did not significantly change the cerebral choline contents in sham rats.

[Choline Acetyltransferase Activities and Acetylcholine Contents]

Figure 6:
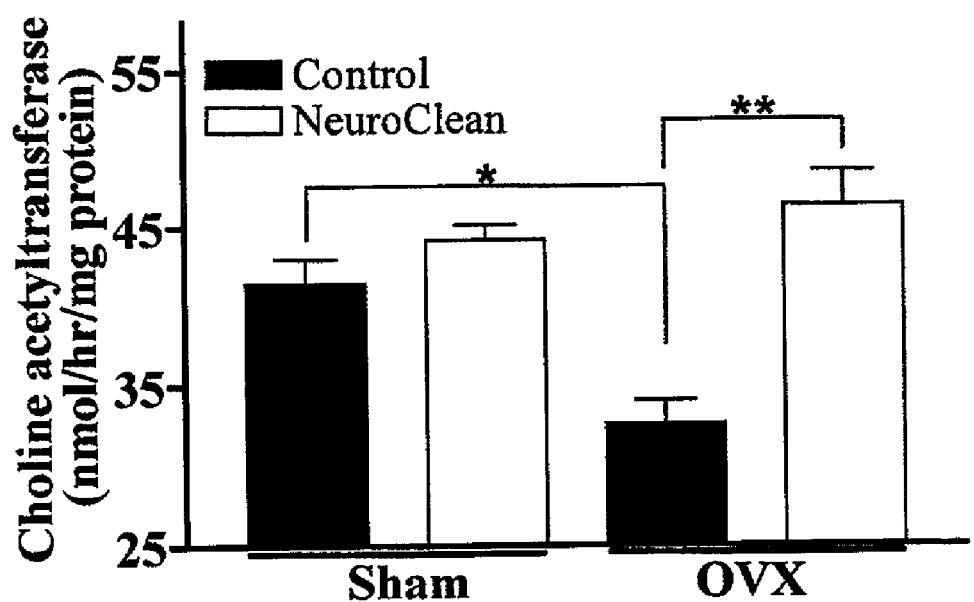
FIG. 6 represents increases of cerebral choline acetyltransferase activities by Neuroclean in OVX rats, where results were expressed as mean±S.E. of 10 rats ((*p<0.05, **p<0.01))

FIG. 6 shows ChAT activities in the frontoparietal cerebral cortex of sham and OVX rats. At 26 weeks after ovariectomy, ChAT activities of cerebral cortex in OVX rats (32.6±1.50 nmol/hr/mg protein) was significantly low compared to those (41.5±1.53) in sham rats ($p<0.05$). The decreased cerebral ChAT activities in OVX rats were completely recovered by treatment of NC for 14 weeks ($p<0.01$). However, NC administration did not change the cerebral ChAT activities in sham rats.

Figure 7:
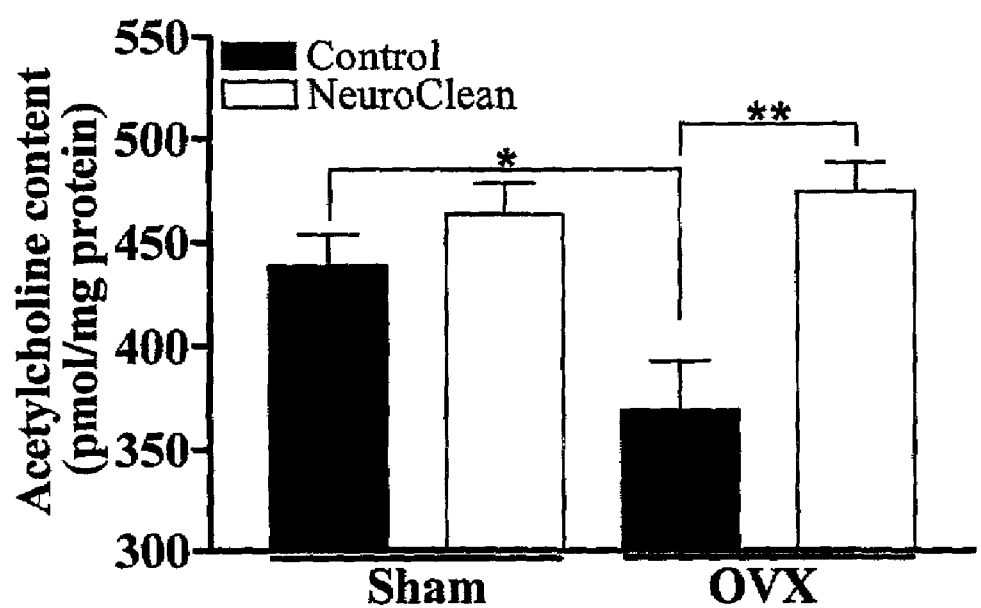
FIG. 7 represents increases of cerebral acetylcholine contents by Neuroclean in OVX rats, where results were expressed as mean±S.E. of 10 rats (*p<0.05, **p<0.01)

As shown in FIG. 7, at 26 weeks after ovariectomy, cerebral ACh content (369.4±23.27 pmol/mg protein) in OVX rats were significantly low compared to that (438.4±15.24) in sham rats ($p<0.05$). These decreases were completely recovered by treatment of OVX rats with NC for 14 weeks ($p<0.01$). However, NC did not affect the change of cerebral ACh contents in sham animals.

In this invention, it is noted that the effects of NC, a newly formulated herbal medicine, on the metabolic pathways of cerebral energy and cholinergic neurotransmitter production in OVX rats as a climacteric disorder model. Superfusion of NC at 50 mg/kg body weight significantly increased the CBF, but not affect to the MABP. Cerebral ATP, choline and ACh contents were markedly decreased by deprivation of ovarian steroid hormones for 26 weeks, and similar phenomenon were also observed in ChAT activitivities of frontoparietal cerebral cortex in OVX rats. Importantly, these reductions were completely restored by treatment of OVX rats with NC at 500 mg/kg body weight per day for 14 weeks. The results obtained in this study suggest a possible pharmacological property of NC, indicating that NC increases the CBF, cerebroneuronal ATP, choline and ACh contents as well as ChAT activities declined by deprivation of ovarian steroid hormones.

Normal, physiological aging of human brain has been associated with cerebral atrophy and neuronal death, and the age-related changes in neuronal system may be due, in part, to hormonal changes (Birge 1997). The present and previous our studies (Ma et al 2000) could observe the decreases of relative cerebral weight to body weight caused by ovariectomy, and decreased cerebral weight was partly recovered by the treatment of OVX rats with NC. In pharmacological regards, this may indicate a possible role of NC in the development of cerebroneuronal abnormalities by hormonal changes. Recent studies suggested that women were at greater risk for AD than man (Gibbs 1998). In incipient late-onset of senile dementia of Alzheimer type (SDAT), cerebral glucose utilization and blood flow are found to be diminished in all areas of the cerebral cortex (Hoyer 1996; Wolf and Grotta 2000). Regarding in these suggestions and a postulated pharmacological property of NC, this study firstly measured the effects of NC on CBF, and observed the increase of CBF by NC superfusion (FIG. 2). In OVX rats, NC treatment did not greatly change serum glucose contents, but significantly elevated cerebral glucose contents ($p<0.05$, data not shown). It is difficult to explain the exact biochemical mechanisms related to the changes of cerebral glucose contents, because the results obtained in this study may be resulted from the complex biochemical pathways associated with a relationship between glucose uptake by enhanced CBF and its utilization. However, we would consider that increases of cerebral glucose contents might be related to an enhanced uptake of glucose through cellular membrane. This hypothesis could be supported by the results shown in FIG. 4, indicating that NC significantly increase the cerebral ATP contents declined by ovariectomy.

A low glucose turnover is able to synthesize a minimal amount of ATP to preserve life (Meier-Ruge et al 1994). The low glucose turnover can lower the ATP production, and this can more pronounce the symptomatology of a dementing brain diseases (Erecinska and Silber 1989; Hoyer 1991). The present study could observe that cerebral ATP contents in OVX rats were diminished by 24% as compared to that in sham animals (FIG. 4). These decreases may be associated with a decline of cerebral glucose turnover by depletion of ovarian steroid hormones, resulting in decreases of cerebral ATP production as demonstrated in the previous reports (Brige 1997; Erecinska and Silber 1989; Hoyer 1991). Interestingly, declined cerebral ATP contents were markedly elevated by treatment of OVX rats with NC. Therefore, we consider that these results may be resulted from the increases of CBF and cerebral glucose turnover by NC, and the pathophysiological role of NC-induced increases of cerebral ATP contents may be related to the maintenance of a variety of cellular functions in the cerebral cortex of OVX rats. Moreover, the facts that NC increases a declined cerebral ATP content in OVX rats suggest the possibility of increased glucose utilization/turnover, followed by possibly increased production of acetyl CoA, which is an essential substrate for ACh synthesis (Sims et al 1981).

In addition, pathological alteration of cerebral choline contents is also involved in the learning and memory loss (Wurtman 1992), because decrease of intracellular choline contents leads to a reduction in ACh production (Soininen et al 1995). Ehrenstein et al. (1997) demonstrated the choline leakage hypothesis for the loss of ACh in the brain with SDAT, and Simpkins et al. (1997) also reported that deficiencies of ovarian steroid hormones caused a decrease of high affinity choline uptake and ChAT activity in frontal cortex and hippocampus. In this study, we observed that deprivation of ovarian steroid hormones for 26 weeks caused a significant decline of cerebral choline and ACh contents in OVX rats, and a similar extent of decrease was also observed in cerebral ChAT activities. These results are closely consistent with the previous results (Ma et al 2000; Torrizuka 2000). Interestingly, the reductions of cerebral choline, ACh content and ChAT activities were significantly recovered by treatment of OVX rats with NC for 14 weeks, suggesting that NC may have a pharmacological role to improve ACh synthesis declined by deprivation of ovarian steroid hormones.

Figure 8:
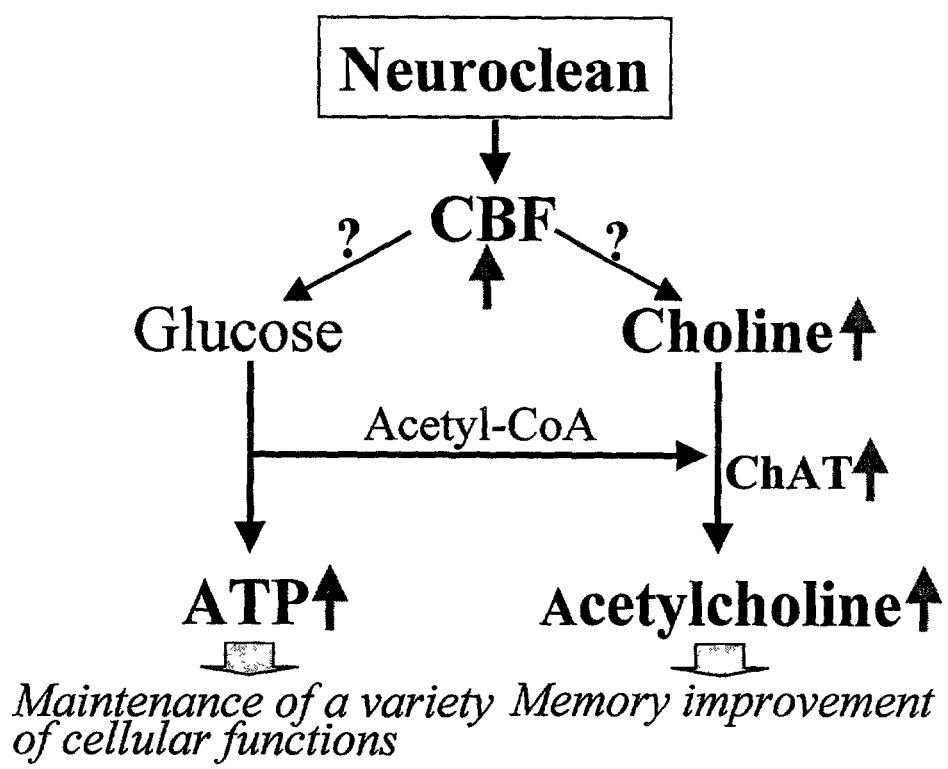
FIG. 8 represents a postulated pharmacological mechanism of Neuroclean to increase cerebroneuronal ATP and ACh contents in OVX rats.

As shown in FIG. 8, we consider four possibilities involved in the pharmacological properties of NC on the cerebroneuronal dysfunctions in OVX rats. First, we consider that NC increases the CBF, and this may affect the metabolic pathways of cerebral glucose turnover, because NC increases cerebroneuronal glucose and ATP contents. Second, the declined cerebral choline contents may be resulted from the decrease of high affinity choline uptake (Simpkins et al 1997) and/or increases of choline-leakage through cell membrane (Ehrenstein et al 1997). These pathological alterations may be recovered, in part, by NC-induced increases of cerebral ATP contents, because the absolute intracellular ATP concentrations are important in the maintenance of cellular physiological processes such as cellular membrane structures, receptor and transporter activities (Erecinska and Silver 1989). Third, NC may increase the ACh contents of frontoparietal cerebral cortex either through a direct action on the ChAT activities decreased by deprivation of ovarian steroid hormones or through indirectly activation of the neuroendocrine processes. Fourth, cerebral ACh contents declined by ovariectomy may be resulted from the decline of cerebral glucose turnover and choline contents, because decreases of cerebral choline and acetyl CoA contents caused by reduction of glucose turnover lead to a reduction in ACh production (Hoyer 1996; Soininen et al 1995). Accordingly, NC would not only accelerate the glucose metabolism to produce cerebral ATP, but also increases the intracellular substrate concentrations to be essentially used for the synthesis of cholinergic neurotransmitter, ACh.

In conclusion, these finding suggest that deprivation of ovarian steroid hormones in rats causes decrease of cerebral ATP, choline, ACh contents and ChAT activities, and these reduction are restored by NC treatment. Therefore, it is conceivable that NC may be a useful medicine for being able to improve learning- and memory-impaired dementia caused by postmenopausal changes and disturbance of cerebral blood circulation.

As described above, the herbal composition of the present invention for the prevention and treatment of dementia comprises *Polygoni multiflori Radix* as a major component instead of ginseng in the conventional herbal composition and further *Polygalae Radix, Caryophylli Flos,* and *Zingibreis Rhizoma* of which components are not added in the conventional composition. This novel composition shows excellent inhibitory activity against dementia with little adverse effects and toxicities.

Therefore, large amount of the herbal composition of the present invention with an appropriate ratio of each component can be administered for long period due to no adverse effects and toxicities therefrom and also it can be applied as nutritional supplement drinks to anybody to prevent and cure dementia.

What is claimed is:

1. A herbal composition for the prevention and treatment of dementia consisting essentially of 10–50 weight parts of *Polygoni multiflori Radix* as a main ingredient, 1–15 weight parts of *Gastrodiae Rhizoma,* 1–10 weight parts of *Acori Graminei Rhizoma,* 1–15 weight parts of *Ostericum Koreanum* or *Curcuma Longae Rhizoma,* 1–8 weight parts of *Caulis Phyllostachyos* or *Folium Phyllostachyos,* 1–8 weight parts of *Bombycis Batryticatus,* 1–8 weight parts of *Fructus immaturus ponciri,* 5–20 weight parts of *Poria,* 2–20 weight parts of *Aurantii nobilis Pericarpium,* 1–5 weight parts of *Glycyrrhizae Radix,* and 1–10 weight parts of *Zingiberis Rhizoma.*

2. The composition of 1, further comprising one or more ingredients chosen from 1–15 weight parts *Arisaematis Rhizoma,* 1–10 weight parts *Pinelliae Tuber,* 2–20 weight parts *Cyperi Rhizoma,* 1–10 weight parts *Saussurea Radix,* 1–10 weight parts *Polygalae Radix,* and 1–10 weight parts *Caryophylli Flos.*

3. The composition of 1 or 2, wherein the ingredient amounts are chosen from one or more of *Glycyrrhizae Radix:* from about 1 to about 2 weight parts; *Pinelliae Tuber* from about 1 to about 4 weight parts; *Aurantii nobilis Pericarpium:* from about 10 to about 20 weight parts; *Gastrodiae Rhizoma:* from about 1 to about 5 weight parts; *Ostericum Koreanum:* from about 1 to about 4 weight parts; *Poria:* from about 16 to about 20 weight parts; *Arisaematis Rhizoma:* from about 1 to about 4 weight parts; *Acori Graminei Rhizoma:* from about 1 to about 4 weight parts; *Bombycis Batryticatus:* from about 1 to about 4 weight parts; *Fructus immaturus ponciri:* from about 1 to about 4 weight parts; and *Caulis Phyllostachyos* or *Folium Phyllostachyos:* from about 1 to about 4 weight parts.

* * * * *

UNITED STATES PATENT AND TRADEMARK OFFICE
CERTIFICATE OF CORRECTION

PATENT NO. : 7,083,811 B2 Page 1 of 1
APPLICATION NO. : 10/053620
DATED : August 1, 2006
INVENTOR(S) : Kyu Yong Jung and Kyung Soo Keum It is certified that error appears in the above-identified patent and that said Letters Patent is hereby corrected as shown below:

In the Claims:

Claim 2, column 20, line 46, "of 1," should read --of claim 1--

Claim 3, column 20, line 52, "of 1 or 2" should read --of claim 1 or 2--

Claim 3, column 20, line 54, after "Tuber" insert --:--

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,083,811 B2 | |
| APPLICATION NO. | : 10/053620 | |
| DATED | : August 1, 2006 | |
| INVENTOR(S) | : Jung et al. | |

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (42) days Delete the phrase "by 42" and insert -- by 16 days--

Signed and Sealed this

Tenth Day of July, 2007

JON W. DUDAS
*Director of the United States Patent and Trademark Office*